United States Patent
Pinsonneault (10) Patent No.: US 7,912,741 B1
(45) Date of Patent: Mar. 22, 2011

(54) SYSTEMS AND METHODS FOR COPAY ADJUSTMENTS

(75) Inventor: Roger Pinsonneault, Alpharetta, GA (US)

(73) Assignee: McKesson Financial Holdings Limited (BM)

( * ) Notice: Subject to any disclaimer, the term of this patent is extended or adjusted under 35 U.S.C. 154(b) by 422 days.

(21) Appl. No.: 12/165,221

(22) Filed: Jun. 30, 2008

(51) Int. Cl.
*G06Q 10/00* (2006.01)

(52) U.S. Cl. .............. 705/4; 705/2; 705/3; 705/14.25; 600/300; 600/301

(58) Field of Classification Search .............. 705/1–5, 705/7–8, 26, 14.25
See application file for complete search history.

(56) References Cited

U.S. PATENT DOCUMENTS

| | | | |
|---|---|---|---|
| 5,628,530 | A | 5/1997 | Thornton |
| 6,012,035 | A | 1/2000 | Freeman et al. |
| 6,757,898 | B1 | 6/2004 | Ilsen et al. |
| 6,769,228 | B1 | 8/2004 | Mahar |
| 7,155,397 | B2 | 12/2006 | Alexander et al. |
| 7,337,129 | B1 | 2/2008 | Lowry et al. |
| 2002/0002495 | A1 | 1/2002 | Ullman |
| 2002/0087583 | A1 | 7/2002 | Morgan et al. |
| 2002/0111832 | A1 | 8/2002 | Judge |
| 2002/0198831 | A1 | 12/2002 | Patricelli et al. |
| 2003/0009367 | A1 | 1/2003 | Morrison |
| 2003/0050799 | A1 | 3/2003 | Jay et al. |
| 2003/0149625 | A1 | 8/2003 | Leonardi et al. |
| 2003/0154163 | A1 | 8/2003 | Phillips et al. |
| 2003/0229540 | A1 | 12/2003 | Algiene |
| 2004/0039599 | A1 | 2/2004 | Fralic |
| 2004/0073457 | A1 | 4/2004 | Kalies |
| 2004/0078234 | A1 | 4/2004 | Tallal, Jr. |
| 2004/0117323 | A1 | 6/2004 | Mindala |
| 2004/0148198 | A1 | 7/2004 | Kalies |
| 2004/0249745 | A1 | 12/2004 | Baaren |
| 2005/0015280 | A1 | 1/2005 | Gabel et al. |
| 2005/0060201 | A1 | 3/2005 | Connely et al. |
| 2005/0102169 | A1 | 5/2005 | Wilson |
| 2005/0154627 | A1 | 7/2005 | Zuzek et al. |

(Continued)

FOREIGN PATENT DOCUMENTS

CA 2482370 3/2006

(Continued)

OTHER PUBLICATIONS

Notice of Allowance for U.S. Appl. No. 12/189,650 mailed Aug. 13, 2010.

(Continued)

*Primary Examiner* — Vivek D Koppikar (74) *Attorney, Agent, or Firm* — Sutherland Asbill & Brennan LLP (57) ABSTRACT

Systems and methods may provide for copay adjustment. The systems and methods may include receiving a claim request from a pharmacy computer, where the claim request may be associated with a product requested by a customer, transmitting the claim request to a claims processor for adjudication, and receiving, from the claims processor, a first claim response for the claim request, where the first claim response may include a current copay amount payable by the customer. The systems and methods may also include determining, based upon a historical claim transaction record associated with the customer, that a prior copay amount for the drug is less than the current copay amount, and transmitting a second claim response to the pharmacy computer with a new copay amount lower than the current copay amount of the first claim response.

22 Claims, 5 Drawing Sheets

U.S. PATENT DOCUMENTS

| | | | |
|---|---|---|---|
| 2005/0187793 | A1 | 8/2005 | Myles |
| 2005/0197862 | A1 | 9/2005 | Paterson et al. |
| 2005/0240473 | A1 | 10/2005 | Ayers |
| 2005/0288972 | A1 | 12/2005 | Marvin et al. |
| 2006/0020514 | A1 | 1/2006 | Yered |
| 2006/0026041 | A1 | 2/2006 | Ullman et al. |
| 2006/0149595 | A1* | 7/2006 | Williams et al. .......... 705/2 |
| 2006/0149784 | A1 | 7/2006 | Tholl et al. |
| 2006/0184391 | A1 | 8/2006 | Barre et al. |
| 2006/0259363 | A1 | 11/2006 | Jhetam |
| 2007/0005402 | A1 | 1/2007 | Kennedy et al. |
| 2007/0050209 | A1 | 3/2007 | Yered |
| 2007/0136100 | A1 | 6/2007 | Daugherty et al. |
| 2007/0233525 | A1 | 10/2007 | Boyle |
| 2007/0233526 | A1 | 10/2007 | Hoffman et al. |
| 2007/0239493 | A1 | 10/2007 | Sweetland et al. |

FOREIGN PATENT DOCUMENTS

| | | |
|---|---|---|
| WO | 9503569 | 2/1995 |
| WO | 0039737 | 7/2000 |
| WO | 2007025295 | 3/2007 |

OTHER PUBLICATIONS www.ncoil.org/news/DrugCards2.doc dated Apr. 2002.

Non-final Office Action for U.S. Appl. No. 12/189,654 mailed Jan. 22, 2010.

Non-final Office Action for U.S. Appl. No. 12/189,650 mailed Jan. 22, 2010.

Sampson, R.J., Taking Control of Health Care Costs, Best's Review—Life Health Insurance Edition, Nov. 1983, pp. 64-66, vol. 84, Issue 7, USA.

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic: On-line Goes In-House, Chain Store Age Exectutive, Jan. 1987, pp. 128-132. vol. 63, Issue 1, USA.

Anonymous, TechRx Announces Successful Beta Deployment of T-Rex. PR Newswire. May 13, 2002.

Notice of Allowance of U.S. Appl. No. 11/674,069 dated Jul. 19, 2010.

* cited by examiner

FIG. 4B

SYSTEMS AND METHODS FOR COPAY ADJUSTMENTS

FIELD OF THE INVENTION

Aspects of the invention relate generally to prescription drugs, medications, over-the-counter drugs, or medical devices (collectively referred to herein as "products") and more particularly, to systems and methods that allow pharmaceutical manufacturers, suppliers, or related entities to encourage acceptance of their products through tailored patient funding.

BACKGROUND OF THE INVENTION

With the increasing costs of drugs and other products, customers as a whole are a highly price-sensitive group. Indeed, studies have shown that the likelihood of a customer purchasing drugs is strongly correlated with the customer's out-of-pocket costs for the drugs or other products. Given that customers are a price-sensitive group, it is not usual to expect that customers may stop taking a drug/product or may switch to a cheaper drug/product if the customer's out-of-pocket cost increases.

In some situations, a pharmaceutical manufacturer or related entity may be willing to subsidize a customer's out-of-pocket costs. However, such subsidies can be very expensive to maintain. Accordingly, there is a need for limiting subsidy costs while still maintaining customers for a drug or other product.

SUMMARY OF THE INVENTION

According to an example embodiment of the invention, there may be a computer-implemented method for copay adjustment. The method may include receiving a claim request from a pharmacy computer, where the claim request may be associated with a product requested by a customer, transmitting the claim request to a claims processor for adjudication, and receiving, from the claims processor, a first claim response for the claim request, where the first claim response may include a current copay amount payable by the customer. The method may also include determining, based upon a historical claim transaction record associated with the customer, that a prior copay amount for the drug is less than the current copay amount, and transmitting a second claim response to the pharmacy computer with a new copay amount lower than the current copay amount of the first claim response.

According to another example embodiment of the invention, there may be a system for copay adjustment. The system may include a memory for storing computer-executable instructions, and a processor. The processor may access the memory and may be configured to execute the computer-executable instructions to receive a claim request from a pharmacy computer, where the claim request may be associated with a product requested by a customer, transmit the claim request to a claims processor for adjudication, and receive, from the claims processor, a first claim response for the claim request, wherein the first claim response may include a current copay amount payable by the customer. The processor may be further configured to execute the computer-executable instructions to determine, based upon a historical claim transaction record associated with the customer, that a prior copay amount for the drug is less than the current copay amount, and transmit a second claim response to the pharmacy computer with a new copay amount lower than the current copay amount of the first claim response.

BRIEF DESCRIPTION OF THE DRAWINGS

Reference will now be made to the accompanying drawings, which are not necessarily drawn to scale, and wherein.

DETAILED DESCRIPTION

Embodiments of the invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments of the invention are described below with reference to block diagrams and flowchart illustrations of systems, methods, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, a processor, a special purpose computer such as a switch, or other programmable data processing apparatus to produce a machine, such that the instructions which execute on the computer or other programmable data processing apparatus create means for implementing the functions specified in the flowchart block or blocks.

These computer program instructions may also be stored in a computer-readable memory that can direct a processor, computer, or other programmable data processing apparatus to function in a particular manner, such that the instructions stored in the computer-readable memory produce an article of manufacture including instruction means that implement the function specified in the flowchart block or blocks. The computer program instructions may also be loaded onto a processor, computer, or other programmable data-processing apparatus to cause a series of operational elements or steps to be performed on the computer or other programmable apparatus to produce a computer-implemented process such that the instructions that execute on the computer or other programmable apparatus provide elements or steps for implementing the functions specified in the flowchart block or blocks.

Accordingly, blocks of the block diagrams and flowchart illustrations may support combinations of means for performing the specified functions, combinations of elements or steps for performing the specified functions, and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions, elements or steps, or combinations of special purpose hardware and computer instructions.

Embodiments of the invention may provide systems and methods by which pharmaceutical manufacturers, or their representatives/distributors/affiliates (which may collectively be referred to as "pharmaceutical manufacturers"), may provide for customer/patient funding for one or more prescription drugs or other products. According to an example embodiment of the invention, prior customer/patient transactions may be stored in a database, perhaps in a history file record in the database. When customer/patient funding opportunities are available, the customer/patient responsible amount may be adjusted depending on the customer/patient's prior customer/patient-responsible amount indicated by the prior customer/patient transactions, which may be readily accessible via the database. Accordingly, by adjusting a customer/patient's copay or customer/patient-responsible amount to what is expected from prior patient transactions, there may be an enhanced adoption rate for the prescription drug.

Figure 1:
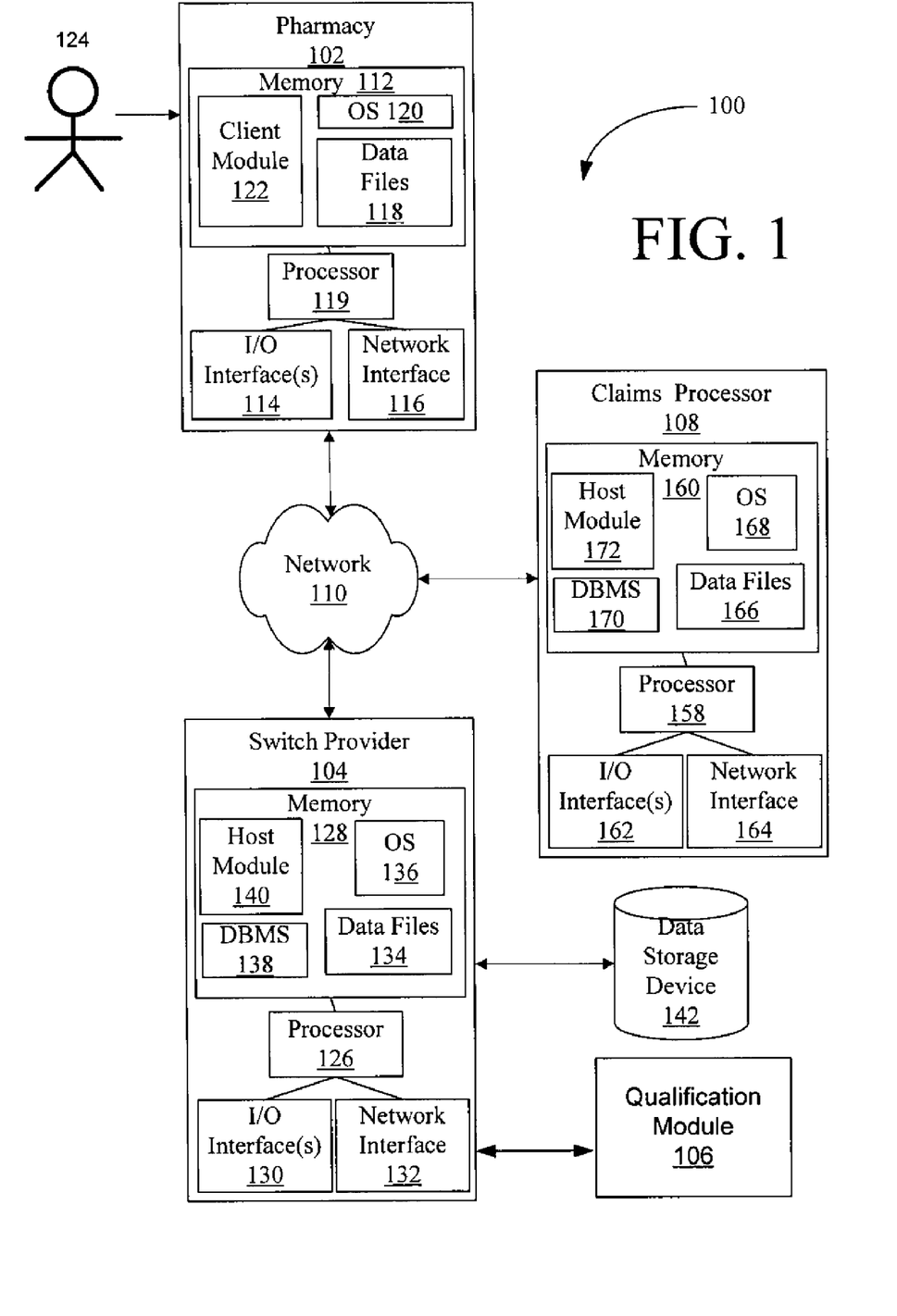
FIG. 1 illustrates an example system that allows for adjustments to customer/patient copay or customer/patient-responsible amounts based upon a history of prior customer/patient transactions, according to an example embodiment of the invention.

FIG. 1 illustrates an example system that allows for adjustments to customer/patient copay or customer/patient-responsible amounts based upon a history of prior customer/patient transactions, according to an example embodiment of the invention. The system 100 may include at least one pharmacy 102 computer, at least one switch provider 104, and a claims processor 108, which are each configured for accessing and reading associated computer-readable media having stored thereon data and/or computer-executable instructions for implementing the various methods of the invention. Generally, the claims processor 108 may determine benefits, coverage, and/or extent of coverage for one or more claims. According to an embodiment of the invention, the claims processor 108 may be associated with a pharmaceutical benefits manager (PBM), an insurance company, or another third-party payor. According to another embodiment of the invention, the claims processor 108 may also include providers of 100% copay plans such as discount programs. The claims processor 108 may be operated by or otherwise included with the switch provider 104, according to an alternative embodiment of the invention.

Generally, network devices and systems, including the one or more pharmacy 102 computers, switch providers 104, and claims processors 108 may have hardware and/or software for transmitting and receiving data and/or computer-executable instructions over a communications link, and a memory for storing data and/or computer-executable instructions. These network devices and systems may also include a processor for processing data and executing computer-executable instructions, as well as other internal and peripheral components that are well known in the art. As used herein, the term "computer-readable medium" may describe any form of memory or a propagated signal transmission medium. Propagated signals representing data and computer-executable instructions may be transferred between network devices and systems.

In FIG. 1, a pharmacy 102 computer may be in communication with the switch provider 104 via a network 110, which as described herein can include one or more private and public networks, whether wired and/or wireless, including the Internet. Likewise, the switch provider 104 may also be in communication with a claims processor 108 via the network 110. According to an embodiment of the invention, the switch provider 104 may form a basis of network 110 for routing communications between the pharmacy 102 computer and the claims processor 108. The switch provider 104 may also include or otherwise be in communication with a qualification module 106 that is operative for determining opportunities for customer/patient funding by a manufacturer for one or more claims, requests, or orders.

The pharmacy 102 computer may be any processor-driven device, such as a personal computer, laptop computer, handheld computer, and the like. In addition to having a processor 119, the pharmacy 102 computer may include a memory 112, input/output ("I/O") interface(s) 114, and a network interface 116. The memory 112 may store data files 118 and various program modules, such as an operating system ("OS") 120 and a client module 122. The client module 122 may be an Internet browser or other software, including a dedicated program, for interacting with the switch provider 104. For example, a user 124 such as a pharmacist or other pharmacy employee, may utilize the client module 122 in preparing and providing a claim, request, or order to the switch provider 104 for processing and/or routing. The pharmacy 102 computer may also utilize the client module 122 to retrieve or otherwise receive data from the switch provider 104, including application or availability of a copay adjustment, voucher, coupon, payment, and/or discount for the claim, request or order, as described herein.

Still referring to the pharmacy 102 computer, the I/O interface(s) 114 may facilitate communication between the processor 119 and various I/O devices, such as a keyboard, mouse, printer, microphone, speaker, monitor, bar code readers/scanners, RFID readers, and the like. The network interface 116 may take any of a number of forms, such as a network interface card, a modem, a wireless network card, and the like. These and other components of the pharmacy 102 computer will be apparent to those of ordinary skill in the art and are therefore not discussed in more detail herein.

The switch provider 104 may include any processor-driven device that is configured for receiving, processing, and fulfilling requests or claims from the pharmacy 102 computer related to pharmacy, benefits, and/or discount transactions, including the copay adjustments, vouchers, coupon, payments, and/or discounts described herein. The switch provider 104 may include a processor 126, a memory 128, input/output ("I/O") interface(s) 130, and a network interface 132. The memory 128 may store data files 134 and various program modules, such as an operating system ("OS") 136, a database management system ("DBMS") 138, and the host module 140. According to an embodiment of the invention, the data files 134 may also store routing tables for determining the subsequent transmission of received claim or request. For example, these routing tables may determine that particular claims or requests are associated with certain payors (e.g., PBMs, insurance companies, etc.), and therefore specify a particular claims processor 108 to route the claim submissions to. The host module 140 may initiate, receive, process, and respond to claims or requests from the respective client module 122 of pharmacy 102 computer, and may further initiate, receive, process, and respond to claims or requests from the host module 172 of the claims processor 108. Likewise, where the qualification module 106 is provided separately from the switch provider 104, the host module 140 may transmit claim information to the qualification module 106, and receive copay adjustment, voucher, coupon, payment and/or discount information from the qualification module 106. It will be appreciated however that in other example embodiments of the invention, the qualification module 106 may also be implemented as part of the switch provider 104, perhaps as computer-executable instructions stored as part of the memory 128.

As illustrated in FIG. 1, the switch provider 104 may also include or be in communication with at least one data storage device 142, or database. If the switch provider 104 includes the data storage device 142, then the data storage device 142 could also be part of the memory 128. The data storage device 142 and/or memory 128 may store, for example, transaction records such as historical claim transaction records and/or adjustments or discounts (e.g., coupons, vouchers, etc.) associated with the claims, requests, and orders. Although a single data storage device 142 is referred to herein for simplicity, those of ordinary skill in the art will appreciate that multiple physical and/or logical data storage devices or databases may be used to store the above mentioned data. For security and performance purposes, the switch provider 104 may have a dedicated connection to the data storage device 142. However, the switch provider 104 may also communicate with the data storage device 142 via a network 110, as shown, or another network. In other embodiments of the invention, the switch provider 104 may include the data storage device 142 locally. The switch provider 104 may also otherwise be part of a distributed or redundant database management system ("DBMS"). It will also be appreciated that the qualification module 106 may likewise access the data storage device 142, either directly or via the switch provider 104.

According to an example embodiment of the invention, the qualification module 106 in FIG. 1 may be comprised of computer-executable instructions for implementing the methods described herein, or variations thereof. The qualification module 106 may be operative to determine opportunities for customer/patient funding by a manufacturer for one or more drug claims, requests, or orders. If there is an opportunity for customer/patient funding, then the qualification module 106 may communicate a copay adjustment, voucher, coupon, payment, and/or discount, or an availability/eligibility determination thereof, to the switch provider 104. In determining the availability/eligibility and/or amount of the copay adjustment, voucher, coupon, payment, and/or discount, the qualification module 106 may access data storage device 142, or otherwise receive information from data storage device 142, to examine prior historical claim transaction records, as described herein.

The claims processor 108 may include any processor-driven device that is configured for receiving, processing, and fulfilling requests from the switch provider 104 related to benefits and/or discount transactions. The claims processor 108 may include a processor 158, a memory 160, input/output ("I/O") interface(s) 162, and a network interface 164. The memory 160 may store data files 166 and various program modules, such as an operating system ("OS") 168, a database management system ("DBMS") 170, and the host module 172. The host module 172 may initiate, receive, process, and respond to requests from the host module 140 of the switch provider 104. The claims processor 108 may include additional program modules for performing other pre-processing or post-processing methods described herein. Those of ordinary skill in the art will appreciate that the claims processor 108 may include alternate and/or additional components, hardware or software.

The network 110 may include any telecommunication and/or data network, whether public, private, or a combination thereof, including a local area network, a wide area network, an intranet, an internet, the Internet, intermediate hand-held data transfer devices, a public switched telephone network (PSTN) and/or any combination thereof and may be wired and/or wireless. The network 110 may also allow for real-time, off-line, and/or batch transactions to be transmitted between the pharmacy 102 computer and the switch provider 104. Due to network connectivity, various methodologies as described herein may be practiced in the context of distributed computing environments. Although the pharmacy 102 computer may be shown for simplicity as being in communication with the switch provider 104 via one intervening network 110, it is to be understood that any other network configuration is possible. For example, intervening network 110 may include a plurality of networks, each with devices such as gateways and routers for providing connectivity between or among networks 110. Instead of or in addition to a network 110, dedicated communication links may be used to connect the various devices of the invention. According to an embodiment of the invention, the network 110 may comprise a network similar to RelayHealth's Intelligent Network.

Those of ordinary skill in the art will appreciate that the system 100 shown in and described with respect to FIG. 1 is provided by way of example only. Numerous other operating environments, system architectures, and device configurations are possible. Accordingly, embodiments of the invention should not be construed as being limited to any particular operating environment, system architecture, or device configuration.

As discussed herein, example embodiments of the invention may provide for customer/patient copay adjustments based upon a history of prior customer/patient transactions, according to an example embodiment of the invention. Example operations of embodiments of the invention will now be described below with reference to FIGS. 2-4.

Figure 2:
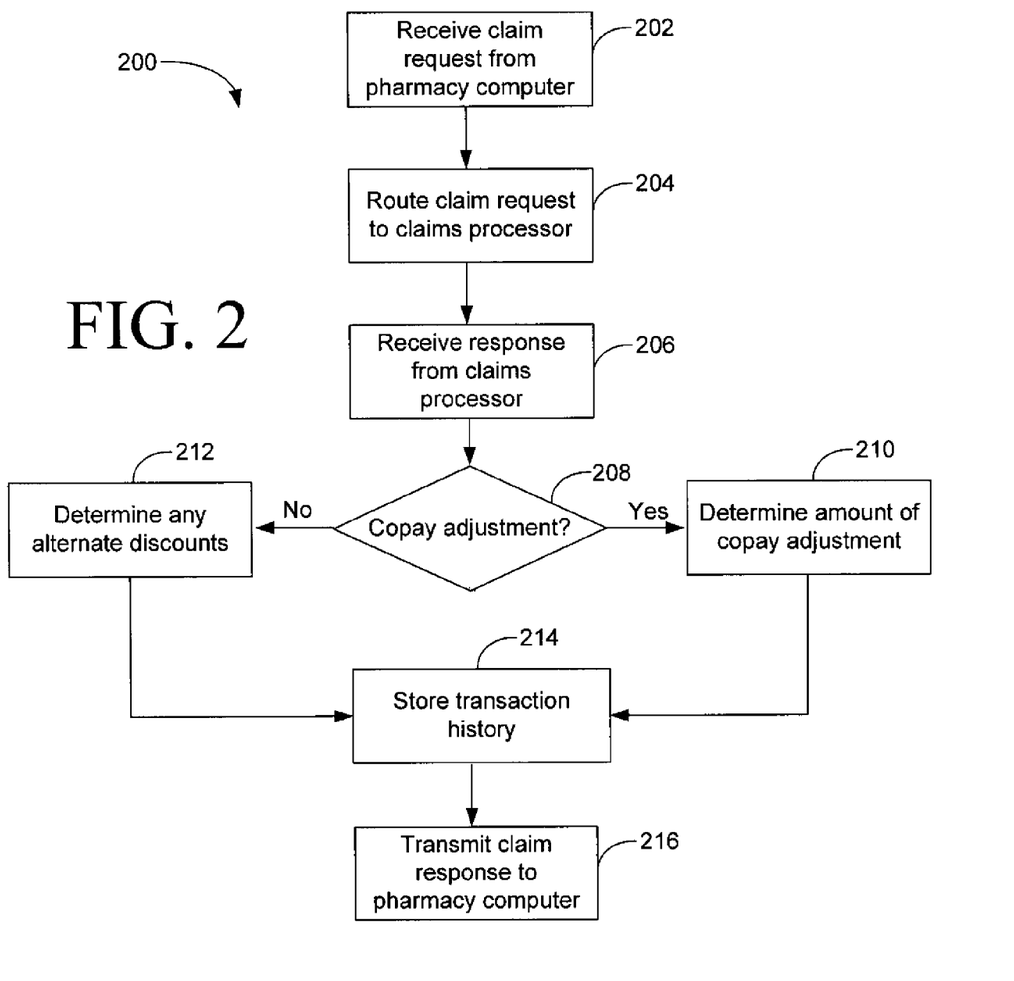
FIG. 2 illustrates an example overview of a method for copay adjustments, according to an example embodiment of the invention.

FIG. 2 illustrates an example overview of a method for copay adjustments, according to an example embodiment of the invention. In block 202, a customer/patient may provide an order for a drug or other product that is entered by a user 124 into the pharmacy 102 computer. The pharmacy 102 computer may then transmit, route, deliver, or otherwise provide a claim request to the switch provider 104. Accordingly, in block 202, the switch provider 104 may receive the claim request from the pharmacy 102 computer. In an example embodiment of the invention, the claim request may include one or more of the following information components:

an identification of the drug (e.g., National Drug Code (NDC)) or other product,
a quantity of the drug or other product,
a price of the drug or other product,
the pharmacy's usual and customary (U&C) price charged for the drug (e.g., a cash customer cost) or other product,
a date of the service, and
a pharmacy identification number.

It will be appreciated that while some example information has been illustrated for the example claim request it will be appreciated that alternate or additional information may also be included without departing from example embodiments of the invention. For example, the claim request may also include a Banking Identification Number (BIN) and a Processor Control Number (PCN) for identifying a claims processor 108 as a destination of the claim request. As another example, the claim request may further include customer/patient identification information. According to an example embodiment of the invention, the customer/patient identification information may include a name, date of birth (DOB), and/or other customer/patient demographic information. According to another embodiment of the invention, the customer/patient identification information may include an identification number, such as a cardholder ID or other patient ID, where the customer/patient may have optionally registered with the switch provider 104 and/or qualification module 106. As part of the registration process, the customer/patient may provide contact information (e.g., a name, address, telephone number, email address, etc.) as well as medical information, such as ailments, conditions, and the like. The customer/patient may then be assigned an identification number following successful registration, according to an example embodiment of the invention. Example registrations may occur via postal mail, telephone, an Internet website/portal, email, and/or in-person at a pharmacy or other registration location. It will be appreciated that the customer/patient registrations may be optional in other example embodiments of the invention.

In block 204, the switch provider 104 may route, transmit, or otherwise deliver the claim request to the claims processor 108 for processing and/or adjudication. According to an example embodiment of the invention, the switch provider 104 may utilize the BIN and PCN in the received claim request to determine which claims processor 108 to route the claim request to. The switch provider 104 may also include a routing table, perhaps stored in memory 128, for determining which claims processor 108 to route the claim request to. According to an example embodiment of the invention, the claims processor 108 may be any claims processing system such as one associated with a pharmacy benefits manager (PBM), an insurance company, or another payor. Alternatively, the third-party processing system 108 may be a discount program processing system, including a discount program where a customer/patient is responsible for paying for a portion or entire cost of the drug.

In block 206, the claims processor 108 may receive and adjudicate the claim request. In particular, the claims processor 108 may determine benefits coverage for the received claim request according to a benefits determination process associated with determining eligibility, pricing, and/or utilization review. According to an example embodiment of the invention, the adjudication or benefits determination process may include determining a covered amount such as an insured amount, as well as a customer/patient-payable amount such as a customer/patient copay amount. According to another example embodiment of the invention, the adjudication or benefits determination process may otherwise include determining a discount amount or discounted price for a drug or other product in accordance with a discount program. In block 206, the claims processor 108 may transmit a claim response to the switch provider 104. If the drug or other product is covered, at least in part, by the claims processor 108, then the claim response generated by the claims processor 108 may include the covered amount, and the customer/patient-payable amount (e.g., customer/patient copay amount or coinsurance amount). If the claim response is provided according to an NCPDP industry standard, then the customer/patient-payable amount may be referred to as a "Patient Pay Amount" where an "Amount of Copay/Co-insurance" may be a component field. The claim response may also include some or all of the information included in the received claim request, as discussed herein. Alternatively, wherein the claims processor 108 is associated with a discount program, the claim response may include the discounted price for a drug or other product in accordance with a discount program. On the other hand, if the drug or other product is not coveted by the claims processor 108, then the claim response may include a rejected claim notice indicating that the drug is not covered by the third-party processing system 108.

In block 208, the switch provider 104 may also provide some or all of the information in the claim response to a qualification module 106 for further determination of eligibility and/or availability of customer/patient copay adjustments. For example, the information provided to the qualification module 106 may include one or more of the following:

an identification of the drug (e.g., National Drug Code (NDC)) or other product, a quantity of the drug or other product, a customer/patient-responsible amount, a customer/patient identifier (e.g., a cardholder ID or other patient ID), a pharmacy identification number, and/or a payor identification number or other identification number associated with the claims processor 108 such as a Banking Identification Number (BIN) and Processor Control Number (PCN).

In block 208, the qualification module 106 may review the received claim information to determine whether an opportunity exists for adjusting the current customer/patient-responsible amount (e.g., copay amount) based upon an analysis of any prior patient transactions similarly involving the requested drug or product (e.g., a historical claim transaction information that may specify a prior copay amount for a drug or product). As an example, if the customer/patient's current copay amount is more than his or her prior copay amount for a quantity of a drug or product, then the qualification module 106 may determine that sufficient manufacturer funding is available to reduce the current copay amount, perhaps down to the prior copay amount. An example copay adjustment logic in accordance with an example embodiment of the invention will be discussed in further detail with respect to FIGS. 3A and 3B.

If block 208 determines that there is an available copay adjustment, then processing may proceed to block 210. In block 210, the qualification module 106 may determine the copay adjustment amount to be provided to the customer/patient, according to an example embodiment of the invention. Alternatively, if block 208 determines that there is no copay adjustment available, perhaps if a historical claim transaction record for the patient and/or drug or product does not exist or if the current copay does not meet certain threshold requirements, then the switch provider 104 may determine whether any other discounts or payments may be available to reduce the customer/patient copay amount or customer/patient-responsible amount. Following blocks 210 or 212, processing may proceed to block 214, where a historical claim transaction record may be recorded in data storage device 142 or another similar database. According to an example embodiment of the invention, a historical claim transaction record may include some or all of the following fields:

Patient ID: an identifier for the patient such as the cardholder's ID,

Payor ID: a BIN Number and PCN that is associated with a payor or claims processor 108, Pharmacy ID: an identifier of the pharmacy 102 originating the claim request, Days Supply: the estimated number of days a prescription will last, Quantity Dispensed: a dispensing quantity for the drug or product, Product/Service ID: an identifier of the drug or product, such as the NDC, Copay: the patient financial responsibility amount based upon adjudication of the prescription claim request by the claims processor 108, and Copay Adjustment: any amount by which the copay has been reduced, and Date of Service: a date identifying when the prescription was filled or service rendered.

Example records of historical claim transactions are shown below in Table I for purpose of illustration. It will be appreciated that the historical claim transaction records may be purged or otherwise be replaced periodically, perhaps based upon the dates of service, according to an example embodiment of the invention. It will also be appreciated that while the historical claim transaction records may be captured during operation of the switch provider 104, the records could also be uploaded into the data storage device 142 from an external source as well.

TABLE I

| Patient ID | Payor ID | Pharmacy ID | Quantity Dispensed | Drug or Product | Co-pay | Copay Adjustment | Date |
|---|---|---|---|---|---|---|---|
| Patient 1 | BIN/PCN 1 | Pharm. 1 | 30 | Drug A | $30 | $10 | MM/DD/YY |
| Patient 1 | BIN/PCN 2 | Pharm. 2 | 90 | Drug A | $60 | $20 | MM/DD/YY |
| Patient 2 | BIN/PCN 1 | Pharm. 3 | 10 | Drug B | $10 | $0 | MM/DD/YY |
| Patient 3 | BIN/PCN 3 | Pharm. 4 | 30 | Drug C | $25 | $5 | MM/DD/YY |
| Patient 4 | BIN/PCN 2 | Pharm. 5 | 12 | Drug D | $40 | $15 | MM/DD/YY |
| ... | | | ... | ... | ... | | ... |

Following block 214, processing may proceed to block 216. In block 216, a claim response, including a new copay amount (also referred to as a "Patient Pay Amount") reflective of any copay adjustments determined in block 210 or other discounts/payments in block 212, may be transmitted from the switch provider 104 to the pharmacy 102 computer. Accordingly, the claim response may include the amount covered by the claims processor 108 as well as the new customer/patient-responsible amount or copay amount that is reflective of any copay adjustments.

Figure 3A:
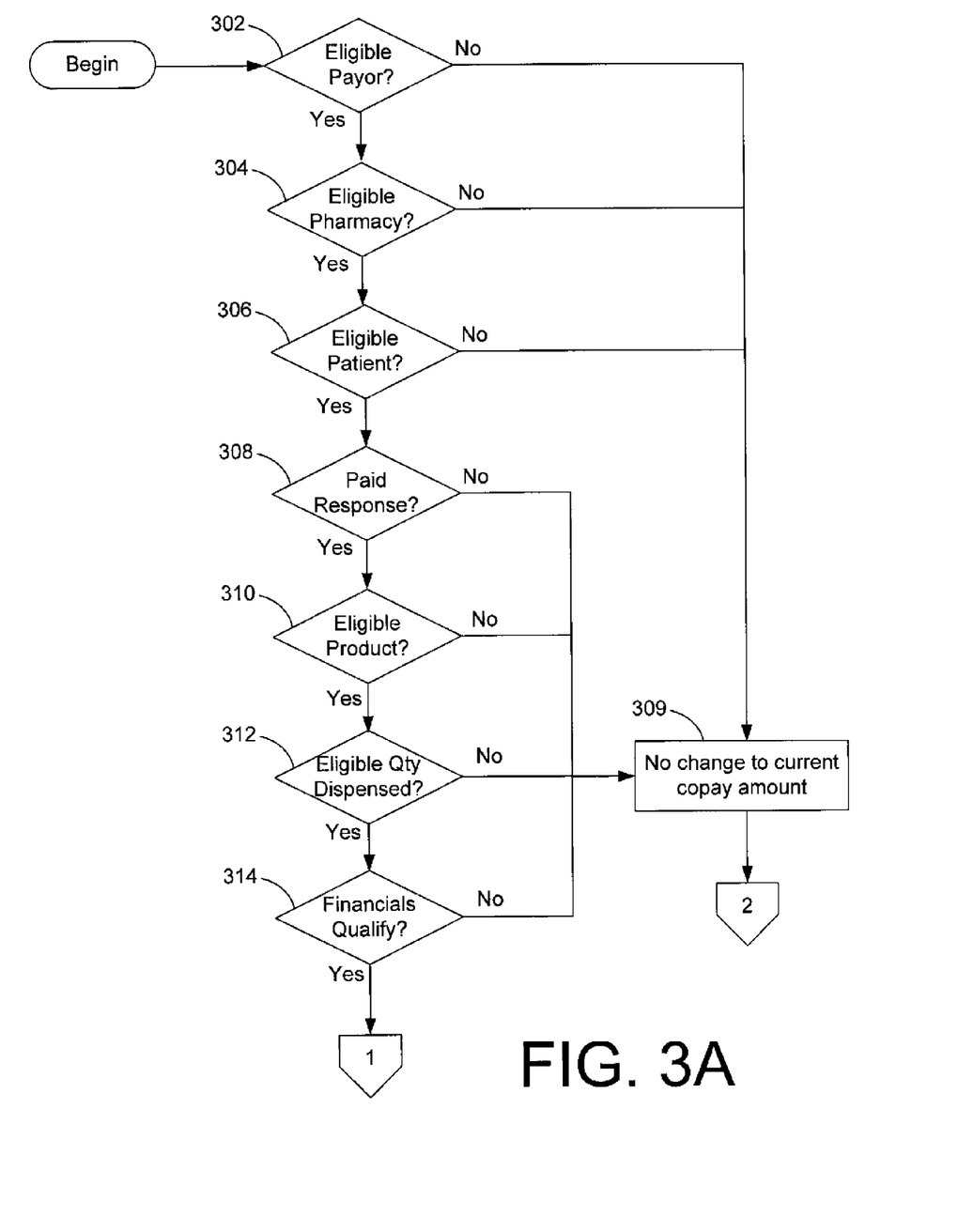
FIGS. 3A and 3B illustrate an example method for customer/patient copay adjustment based upon an analysis of one or more prior copay amounts for a customer/patient, according to an example embodiment of the invention.
Figure 3B:
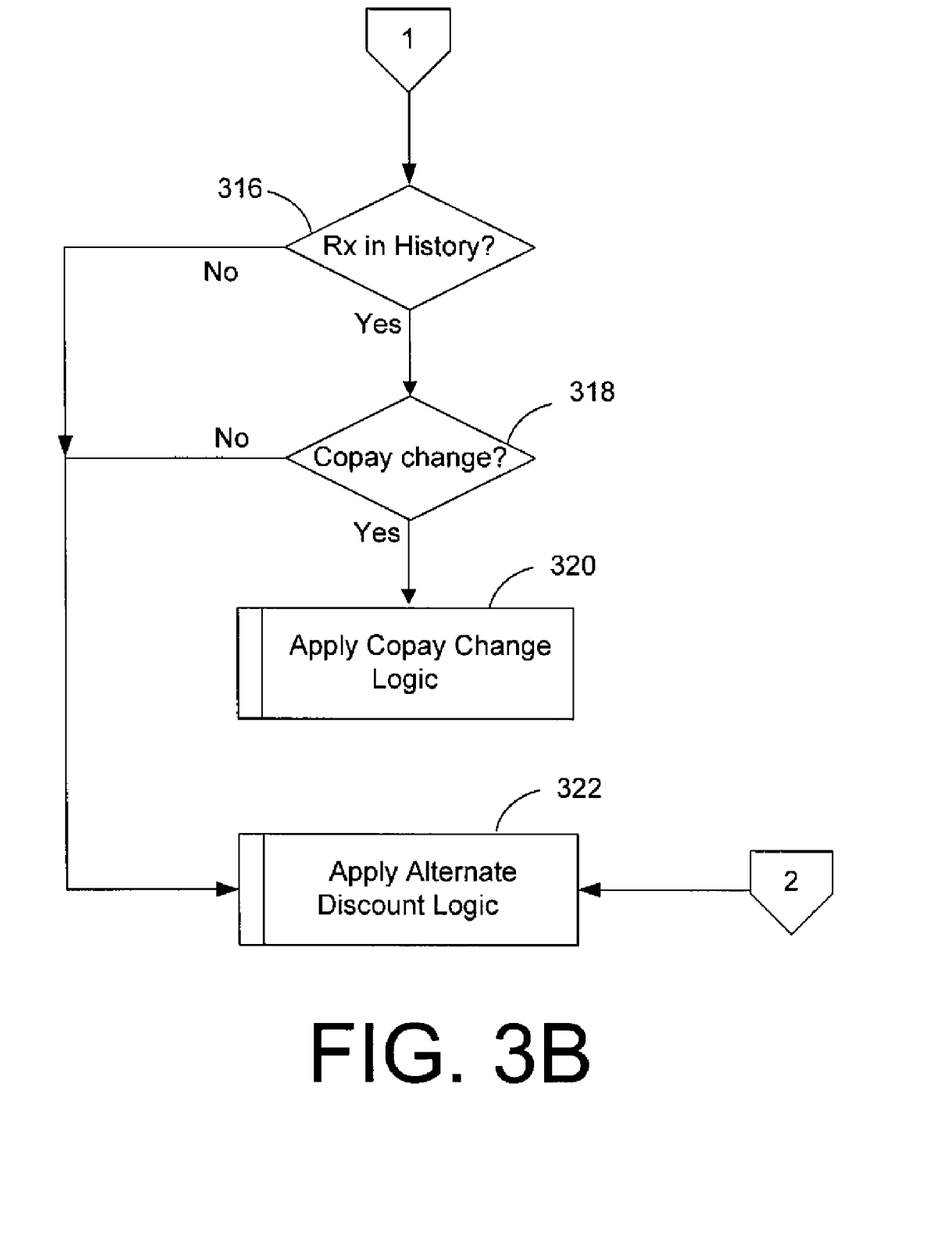

FIGS. 3A and 3B illustrate an example method for determining customer/patient copay adjustments based upon an analysis of prior copay amounts for a customer/patient, according to an example embodiment of the invention. As shown in FIG. 3A, eligibility for a copay adjustment may be based upon eligibility factors associated with a payor (e.g., block 302), the pharmacy (e.g., block 304), the patient (e.g., block 306), the claims processor (e.g., block 308), and/or the requested drug or other product (e.g., blocks 310, 312, 314).

In block 302, the qualification module 106 may determine whether there is an eligible payor involved in the claim transaction. In an example embodiment of the invention, the qualification module 106 may determine that a payor is eligible by comparing the BIN and PCN in the received claim information to a list of eligible BIN and PCN's. Block 304 may determine whether an eligible pharmacy is involved in the claim transaction. In an example embodiment of the invention, the qualification module 106 may determine that a pharmacy is eligible by comparing the submitter ID or pharmacy ID in the received claim information to a list of eligible submitter IDs or pharmacy IDs. Block 306 may determine whether an eligible patient is involved in the claim transaction. In an example embodiment of the invention, the qualification module 106 may determine that the patient is eligible by comparing the patient information in the received claim information (e.g., patient name, patient DOB, and/or patient/cardholder ID) to a list of eligible patients that includes the same information.

In block 308, the qualification module 106 may determine whether a paid response was received from the claims processor 108. In an example embodiment of the invention, a paid response may determined based upon the received claim information specifying a covered amount from the claims processor 108. In block 310, the qualification module 106 may determine whether an eligible product is involved in the claim transaction. Where the product is a drug, the qualification module 106 may compare the product or service identifier such as an NDC received in the claim information to a list of NDCs associated with eligible drugs.

In block 312, the qualification module 106 may optionally determine whether there is there is an eligible quantity being dispensed. According to an example embodiment of the invention, the quantity dispensed may be almost any value for one or more drugs or products, according to an example embodiment of the invention. It will be appreciated that in addition or in the alternative, the qualification module 106 may likewise determine whether there is an eligible days supply being specified in the received claim information.

In block 314, the qualification module 106 may determine whether the financial information in the received claim information is qualified for a copay adjustment. In an example embodiment of the invention, block 314 may involve determining whether the customer/patient copay amount or the customer/patient-responsible amount exceeds one or more thresholds. As an example, block 314 may determine if the customer/patient copay amount or customer/patient-responsible amount exceeds the minimum threshold for a copay adjustment. Alternatively or additionally, block 314 may also determine if the customer/patient copay amount or customer/patient-responsible amount exceeds the maximum threshold to apply a copay adjustment.

If any of the eligibility factors in blocks 302-314 are not satisfied, then there may be no change to the current copay amount according to a copay change logic based upon the analysis of prior copay amounts for a customer/patient, as illustrated by block 309. However, it will appreciated that processing may also proceed to block 322 to determine whether any other discounts or payments may be available according to an alternate discount logic. Likewise, it will be appreciated that in example embodiments of the invention, some or all of the eligibility factors in blocks 302-314 may be optional or provided in a different order than that shown in FIG. 3A.

If blocks 302-314 are satisfied, then processing may proceed to block 316 in FIG. 3B. In block 316, the qualification module 106 may determine whether the requested product and/or associated data (e.g., quantity dispensed, etc.) in the received claim information is associated with a similar prior transaction for the customer/patient. As an example, block 316 may determine whether the customer/patient is associated with any stored historical claim transaction records based upon the received Cardholder ID and/or other patient information of the claim information. Likewise, for any stored historical transaction records located for the customer/patient, block 316 may also determine whether the requested product (e.g., NDC for a drug) and the quantity dispensed in the received claim information matches the product information (e.g., NDC) and quantity dispensed in the stored historical transaction records. It will be appreciated that block 316 may likewise involve determining whether other data in the received claim information matches other data in the stored historical transaction records.

If block 316 determines that the requested product and/or associated data is associated with a similar prior transaction for the customer/patient, then processing may proceed to block 318. In block 318, the qualification module 106 may determine whether a copay change opportunity exists. As an example, in block 318, the qualification module 106 may determine whether the current customer/patient copay amount in the received claim information exceeds the prior customer/patient copay amount in the stored historical claim transaction record. In an example embodiment of the invention, the difference between the current customer/patient copay amount and the prior customer/patient copay amount may need to be within a particular range or percentage. If there is a copay change opportunity in block 318, then processing may proceed to block 320 determining the extent to which a copay adjustment may be available. An example embodiment of the processing in block 320 will be discussed with reference to FIG. 4A.

Alternatively, it will be appreciated that block 316 may determine that the requested product and/or associated data in the current claim transaction is not associated with a similar prior transaction for the customer/patient. Likewise, block 318 may determine that there is not a copay change opportunity. In either case, processing may proceed to block 322, where an alternate discount logic may be applied if available. An example embodiment of the processing in block 322 will be discussed with reference to FIG. 4B.

Figure 4A:
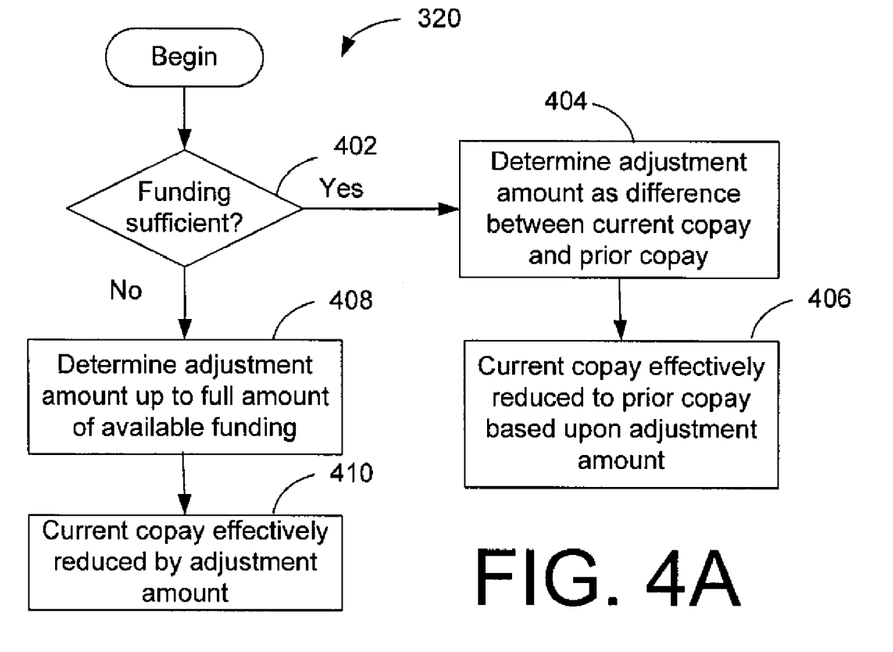
FIG. 4A illustrates an example copay change logic, according to an example embodiment of the invention.

FIG. 4A illustrates an example method for a copay change logic, according to an example embodiment of the invention. As shown in FIG. 4A, processing may begin in block 402 with a qualification module 106 determining whether funding is sufficient to cover a difference between a current copay amount in the received claim information and a prior copay amount in the located transaction history record. If the funding is sufficient in block 402, then processing may proceed with block 404 determining the copay adjustment amount as the difference between the current copay and the prior copay. In block 406, the customer/patient copay amount may then be effectively reduced to the prior copay amount based upon the copay adjustment amount.

On the other hand, block 402 may determine that funding is not sufficient to cover a difference between a current copay amount in the received claim information and a prior copay amount in the located transaction history record, then processing may proceed to block 408. In block 408, the qualification module 106 may determine a copay adjustment amount up to the full amount of available funding (e.g., a maximum discount amount). In block 410, the copay amount may effectively be reduced by the copay adjustment amount.

Figure 4B:
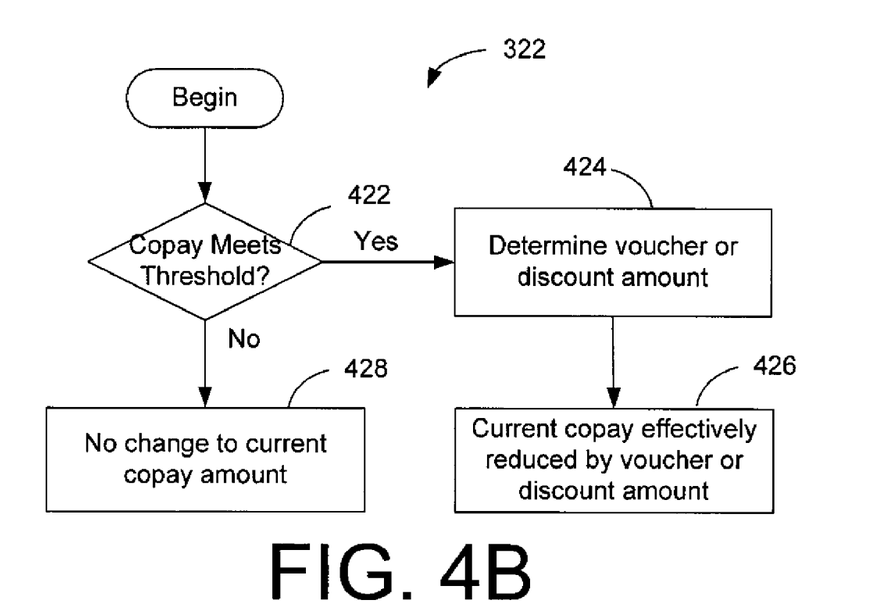
FIG. 4B illustrates an alternate discount logic, according to an example embodiment of the invention.

FIG. 4B illustrates an alternate discount logic, according to an example embodiment of the invention. In block 422, FIG. 4B, the qualification module 106 or another similar module may determine whether the current copay amount in the claim information meets one or more thresholds. According to an example embodiment of the invention, the threshold may be a minimum threshold or a maximum threshold. Accordingly, the current copay amount may need to exceed (or equal) the minimum threshold and/or be lower than (or equal) the maximum threshold in an example embodiment of the invention If the current copay amount does meet one or more thresholds, then processing may proceed with block 424 determining the voucher or discount amount. According to an example embodiment of the invention, the discount or voucher amount may be a predetermined amount or percentage. The discount or voucher amounts may likewise be subject to a minimum and/or maximum discount amount, according to an example embodiment of the invention. In block 426, the current copay is effectively reduced by voucher or discount amount. On the other hand, if the current copay amount does not meet one or more thresholds, then processing may proceed with block 428 determining that there is no change to the current copay amount.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A computer-implemented method for patient-payable amount adjustment, comprising:
   receiving a claim request from a pharmacy computer, wherein the claim request is associated with a drug or prescription product requested by a customer;
   transmitting the claim request to a claims processor for adjudication;
   receiving, from the claims processor, a first claim response for the claim request, wherein the first claim response includes a current patient-payable amount payable by the customer;
   determining, based upon a historical claim transaction record associated with the customer, that a prior patient-payable amount for the drug or prescription product is less than the current patient-payable amount;
   preparing a second claim response based upon determining that the prior patient-payable amount is less than the current patient-payable amount, wherein the second claim response differs from the first claim response in at least that the second claim response includes a new patient-payable amount lower than the current patient-payable amount of the first claim response; and
   transmitting the second claim response to the pharmacy computer, the second claim response being responsive to the received claim request,
   wherein the prior steps are performed by one or more intermediary provider computers.

2. The computer-implemented method of claim 1, wherein the new patient-payable amount is equal to the prior patient-payable amount.

3. The computer-implemented method of claim 1, wherein the drug or prescription product is a prescription drug, and wherein the claim request includes a first identifier for the prescription drug and a second identifier for the customer.

4. The computer-implemented method of claim 3, wherein the historical claim transaction record includes the first identifier for the prescription drug and the second identifier for the customer.

5. The computer-implemented method of claim 4, wherein the request further includes a third identifier associated with a dispensed quantity of the prescription drug, and wherein the historical claim transaction record further includes the third identifier associated with the dispensed quantity.

6. The computer-implemented method of claim 1, wherein prior to transmitting the second claim response, the method further includes determining that the claim response is eligible for patient-payable amount adjustment based upon determining one or both of an eligible pharmacy associated with the pharmacy computer or an eligible payor associated with the claims processor, wherein the prior step is performed by one or more intermediary provider computers.

7. The computer-implemented method of claim 1, further comprising storing a second historical claim transaction record, wherein the second historical claim transaction record includes at least the requested product and information associated with the new patient-payable amount, wherein the prior step is performed by one or more intermediary provider computers.

8. The computer-implemented method of claim 1, further comprising determining a patient-payable adjustment amount based upon a difference between the current patient-payable amount and the prior patient-payable amount, wherein the prior step is performed by one or more intermediary provider computers.

9. The computer-implemented method of claim 8, wherein the new patient-payable amount reflects the patient-payable adjustment amount.

10. The computer-implemented method of claim 8, wherein a maximum discount amount is less than the difference between the current patient-payable amount and the prior patient-payable amount, and wherein the new patient-payable amount is the current patient-payable amount reduced by up to the maximum discount amount.

11. A system for patient-payable amount adjustment, comprising:
a memory for storing computer-executable instructions;
a processor for accessing the memory and configured to execute the computer-executable instructions to:
receive a claim request from a pharmacy computer, wherein the claim request is associated with a drug or prescription product requested by a customer;
transmit the claim request to a claims processor for adjudication;
receive, from the claims processor, a first claim response for the claim request, wherein the first claim response includes a current patient-payable amount payable by the customer;
determine, based upon a historical claim transaction record associated with the customer, that a prior patient-payable amount for the drug or prescription product is less than the current patient-payable amount;
prepare a second claim response based upon the determination that the prior patient-payable amount is less than the current patient-payable amount, wherein the second claim response differs from the first claim response in at least that the second claim response includes a new patient-payable amount lower than the current patient-payable amount of the first claim response; and
transmit the second claim response to the pharmacy computer, the second claim response being responsive to the received claim request.

12. The system of claim 11, wherein the new patient-payable amount is equal to the prior patient-payable amount.

13. The system of claim 11, wherein the drug or prescription product is a prescription drug, and wherein the claim request includes a first identifier for the prescription drug and a second identifier for the customer.

14. The system of claim 13, wherein the historical claim transaction record includes the first identifier for the prescription drug and the second identifier for the customer.

15. The system of claim 14, wherein the request further includes a third identifier associated with a dispensed quantity of the prescription drug, and wherein the historical claim transaction record further includes the third identifier associated with the dispensed quantity.

16. The system of claim 11, wherein prior to transmitting the second claim response, the processor is further configured to execute the computer-executable instructions to determine that the claim response is eligible for patient-payable amount adjustment based upon determining one or both of an eligible pharmacy associated with the pharmacy computer or an eligible payor associated with the claims processor.

17. The system of claim 11, wherein the processor is further configured to execute the computer-executable instructions to store, in the memory, a second historical claim transaction record, wherein the second historical claim transaction record includes at least the requested product and information associated with the new patient-payable amount.

18. The system of claim 11, wherein the processor is further configured to execute the computer-executable instructions to determine a patient-payable adjustment amount based upon a difference between the current patient-payable amount and the prior patient-payable amount.

19. The system of claim 18, wherein the new patient-payable amount reflects the patient-payable adjustment amount.

20. The system of claim 18, wherein a maximum discount amount is less than the difference between the current patient-payable amount and the prior patient-payable amount, and wherein the new patient-payable amount is the current patient-payable amount reduced by up to the maximum discount amount.

21. The computer-implemented method of claim 1, wherein the current patient-payable amount and the new patient-payable amount are respective co-pay amounts.

22. The system of claim 11, wherein the current patient-payable amount and the new patient-payable amount are respective co-pay amounts.

* * * * *